United States Patent [19]
Hori et al.

[11] Patent Number: 5,814,032
[45] Date of Patent: Sep. 29, 1998

[54] PERCUTANEOUS ADMINISTRATION TAPE PREPARATION

[75] Inventors: Mitsuhiko Hori; Katsuhiro Yamamoto; Tetsuo Watanabe, all of Osaka, Japan

[73] Assignee: Nitto Denko Corporation, Osaka, Japan

[21] Appl. No.: 855,897

[22] Filed: May 12, 1997

Related U.S. Application Data

[63] Continuation of Ser. No. 375,984, Jan. 20, 1995, abandoned.

[30] Foreign Application Priority Data

Jan. 21, 1994  [JP]  Japan ................................... 6-004908

[51] Int. Cl.⁶ .............................. A61F 13/02; B32B 9/04
[52] U.S. Cl. ......................... 604/307; 604/304; 424/448
[58] Field of Search ................................... 604/289, 304, 604/305, 307; 424/447–449

[56] References Cited

U.S. PATENT DOCUMENTS

| | | | |
|---|---|---|---|
| 3,734,097 | 5/1973 | Zefferoni | 604/304 |
| 5,059,189 | 10/1991 | Cilento et al. | 604/307 |
| 5,077,055 | 12/1991 | Muller | 424/449 |
| 5,100,672 | 3/1992 | Gueret et al. | 424/449 |

FOREIGN PATENT DOCUMENTS

| | | |
|---|---|---|
| 0130061 | 1/1985 | European Pat. Off. . |
| 0186019 | 7/1986 | European Pat. Off. . |
| 0272149 | 6/1988 | European Pat. Off. . |
| 0303445 | 2/1989 | European Pat. Off. . |
| 0307189 | 3/1989 | European Pat. Off. . |
| 0343807 | 11/1989 | European Pat. Off. . |
| 0379933 | 8/1990 | European Pat. Off. . |
| 0412869 | 2/1991 | European Pat. Off. . |
| 0436203 | 7/1991 | European Pat. Off. . |

OTHER PUBLICATIONS

Y. Lurton et al., "Comparative Study of Seven Hydrocolloid Dressings", vol. 11, 1992, pp. 278–284.
"Dictionnaire Vidal 1993", *Edtions du Vidal*, pp. 28 & 12.
"Patent Abstracts of Japan" vol. 17, No. 158. (Corresponding to JP–A–04,321,623).

*Primary Examiner*—Mark O. Polutta
*Attorney, Agent, or Firm*—Sughrue, Mion, Zinn, Macpeak & Seas, PLLC

[57] ABSTRACT

There provided a percutaneous administration tape preparation which can attach well to the skin surface even in the case of the permeation of water after attaching and can be easily detached from the skin surface without giving the skin simulation such as peeling off and the injury of the horny layer. The percutaneous administration tape preparation comprises a sheet-form support, a drug-containing pressure-sensitive adhesive layer, and a separator, wherein the drug-containing pressure-sensitive adhesive layer comprises a uniform dispersed state containing from 50 to 95% by weight one or more kinds of elastomers, from 5 to 50% by weight a hygroscopic material, and a percutaneous absorption drug so that a part of the hygroscopic material contained therein remains on the applied surface at detaching the tape preparation from the applied surface.

3 Claims, No Drawings

PERCUTANEOUS ADMINISTRATION TAPE PREPARATION

This is a Continuation of application No. 08/375,984 filed Jan. 20, 1995 now abandoned.

FIELD OF THE INVENTION

The present invention relates to a percutaneous administration tape preparation, and more specifically to a percutaneous administration tape preparation giving reduced skin irritation without causing peeling off and injury of the horny layer when the tape is detached from the skin surface.

BACKGROUND OF THE INVENTION

As a method of administrating a drug in a body by a percutaneous administration from the skin surface, a method of using an ointment, a cream agent, a spray agent, etc., have been used from of old, but recently various so-called pressure-sensitive adhesive tape-form preparations each containing a drug in the pressure-sensitive adhesive have been proposed and some kinds of the preparations are on the market. Such a pressure-sensitive adhesive tape-form preparation has various advantages including simplicity of the use thereof, good durability for the effect of medicine, reduced occurrence of side effects, causing no first pass effect in the liver, etc.

However, since such a tape-form preparation is usually attached on the skin surface for a long time, sometimes while perspiring or bathing, water permeates into the tape-form preparation lowering the adhesive force to the skin, whereby the tape is released during use. Accordingly, it is necessary to properly increase the adhesive force of the tape preparation to the skin, but if the adhesive force is too strong, when the preparation is detached from the skin surface, the horny layer is peeled off and injured and liable to cause the skin irritation. Practically, the control of the adhesive force of the pressure-sensitive adhesive tape preparation to the skin is very difficult.

SUMMARY OF THE INVENTION

The present invention has been made for solving the problems of the foregoing conventional pressure-sensitive adhesive tape-form preparation and the object of the present invention is to provide a percutaneous administration tape preparation which can attach well to the skin surface even in the case of the permeation of water after attaching, and can be easily detached from the skin surface without causing skin irritation such as peeling off and injury to the horny layer.

As a result of various investigations for attaining the object described above, the inventors have discovered that by forming the pressure-sensitive adhesive layer containing a drug with at least a specific amount of an elastomer and a specific amount of a hygroscopic material, making moisture absorb into the hygroscopic material while attaching the preparation, and when the preparation is detached from the skin surface, leaving a part of the hygroscopic material having absorbed water on the skin surface, a tape preparation excellent in both the characteristics of the skin adhesive property and the low skin irritating property at detaching is obtained, and have accomplished the present invention based on this discovery.

That is, according to the present invention, there is provided a percutaneous administration tape preparation composed of a sheet-form support, a drug-containing pressure-sensitive adhesive layer, and a separator, wherein the drug-containing pressure-sensitive adhesive layer comprises a uniform dispersion state containing from 50 to 95% by weight of one or more kinds of elastomers, from 5 to 50% by weight a hygroscopic material, and a percutaneous administration drug so that a part of the hygroscopic material contained therein remains on the applied surface at detaching the tape preparation from the applied surface.

DETAILED DESCRIPTION OF THE INVENTION

Then, the present invention is described in detail.

The sheet-form support being used for the percutaneous administration tape preparation of the present invention is for supporting the drug-containing pressure-sensitive adhesive layer on one surface thereof for being attached to the skin surface, and from the points of giving a self-supporting property of the tape preparation (an improvement of an attaching operation property) and preventing the occurrence of a stiff feeling after attaching, a support having a thickness of about from 5 to 25 $\mu$m is usually used. As such a support, various plastic films composed of a polyester, a polyolefin, polyvinyl chloride, polyvinylidene chloride, an ethylene/vinyl acetate copolymer, a polyurethane, etc., a pulp, a metal foil, or composite films formed by laminating the foregoing materials can be used.

In these films, for preventing the drug contained in the pressure-sensitive adhesive layer from dissolving, transferring into the support, and striking through the support to lower the effective amount of the drug, a support having a not transferring property of the drug, such as a polyester, a metal foil, etc., is preferably used. Also, as the support, not only the non-porous sheets but also perforated sheets formed by applying perforation working such as punching, needling, etc., to the non-porous sheets, foamed sheets such as closed cellular, continuous cellular, or semi-continuous cellular sheets, woven fabrics, nonwoven fabrics, knitted cloths, and porous fibrous sheets using hollow fiber yarns, etc., can be used.

Examples of the separator which can be used for the percutaneous administration tape preparation of the present invention include a base sheet subjected to releasing treatment by using a release treating agent such as a silicone resin. Example of the base sheet include a paper and a plastic sheet. The thickness of the base sheet is generally from 10 to 100 $\mu$m, preferably from 20 to 75 $\mu$m.

The drug-containing pressure-sensitive adhesive layer of the present invention generally has a thickness of from 10 to 500 $\mu$m, preferably from 20 to 300 $\mu$m.

The drug-containing pressure-sensitive adhesive layer being formed on one surface of the support is a layer composed of a pressure-sensitive adhesive composition containing percutaneous administration drug(s) for carrying out the prophylaxis and treatment of various kinds of diseases. There is no particular restriction on the percutaneous administration drugs being contained in the pressure-sensitive adhesive composition so long as the drugs can practically perform the prophylaxis and treatment of various diseases by a percutaneous administration. The following drugs are illustrated.

a) Corticosteroids: For example, there are cortisone, hydrocortisone, predonisolone, beclomethasone propionate, dexamethasone, betamethasone, flumethasone, triamcinolone, triamcinolone acetonide, fluocinolone, fluocinolone acetonide, fluocinolone acetonide acetate and clobetasol propionate.

b) Analgesic anti-inflammatory agents: For example, there are acetaminophen, mefenamic acid, flufenamic acid, indomethacin, diclofenac, diclofenac sodium, alclofenac, ibufenac, oxyphenbutazone, phenylbutazone, ibuprofen, flurbiprofen, ketoprofen, salicylic acid, methyl salicylate, 1-menthol, camphor, slindac, tolmetin sodium, napoxen, and fenbufen.

c) Hypnotic sedatives: For example, there are phenobarbital, amobarbital, cyclobarbital, lorazepam, and haloperidol.

d) Tranquilizers: For example, there are fulphenazine, thioridazine, diazepam, flurazepam, and chlorpromazine.

e) Antihypertensives: For example, there are clonidine, clonidine hydrochloride, bopindolol, timolol, pindolol, propranolol, propranolol hydrochloride, bupranolol, indenolol, bucumolol, nifedipine, and bunitrolol.

f) Hypotensive diuretics: For example, there are bendroflumethiazide, polythiazide, methychlothiazide, trichlormethiazide, cyclopenthiazide, benzyl hydrochlorothiazide, hydrochlorothiazide, and bumetanide.

g) Antibiotics: For example, there are penicillin, tethacycline, oxytetracycline, metacycline, doxycycline, minocycline, fradiomycin sulfate, erythromycin, and chloramphenicol.

h) Anesthetics: For example, there are lidocaine, benzocaine, and ethyl aminobenzoate.

i) Antimicrobial agents: For example, there are benzalkonium chloride, nitrofurazone, nystatin, sulfacetamide, and clotriamazole.

j) Antifungal agents: For example, there are pentamycin, amphotericin B, pyrrol nitrin, and clotrimazole.

k) Vitamins: For example, there are vitamin A, ergocalciferol, cholecalciferol, octotiamine, and riboflavin butyric acid ester.

l) Antiepileptics: For example, there are nitrazepam, meprobamate, and clonazepam.

m) Antihistaminics: For example, there are diphenhydramine hydrochloride, chlorpheniramine, and diphenylimidazole.

n) Antitussives: For example, there are dextromethorphan, terbutaline, ephedrine, and ephedrine hydrochloride.

o) Sex hormones: For example, there are progesterone, estradiol, estriol, and estrone.

p) Antidepressants: For example, there is doxepin.

q) Vasodilators: For example, there are nitroglycerin, isosorbide dinitrate, nitroglycol, pentaerythritol tetranitrate, and dipyridamole.

r) Other drugs: For example, there are 5-fluorouracil, dihydroergotamine, fentanyl, desmopressin, digoxin, methoclopramide, domperidone, scopolamine, and scopolamine hydrobromide.

These percutaneous administration drugs can be, if necessary, used as a mixture of two or more kinds thereof. The content of the foregoing drug(s) can be optionally selected according to the drug-releasing faculty of the pressure-sensitive adhesive layer, the kind of the drug(s), the medical effect, etc., but the content thereof is generally in the range of from about 0.01 to 20 parts by weight per 100 parts by weight of the sum total of the elastomer(s) and the hygroscopic material mainly constituting the pressure-sensitive adhesive layer.

From 50 to 95% by weight of the pressure-sensitive adhesive layer is composed of one or more kinds of elastomers. The elastomer is used for imparting a shape-retention property by a proper cohesive force to the pressure-sensitive adhesive layer and is preferably compounded in the range of from 50 to 80% by weight.

Examples of such elastomers which can be used are synthetic rubbers such as polyisobutylene, polyisoprene, polybutadiene, etc.; block copolymer rubbers such as a styrene/isoprene/styrene block copolymer rubber, a styrene/butadiene/styrene block copolymer rubber, etc.; natural rubbers, an acrylic polymer obtained by polymerizing a (meta)acrylic acid alkyl ester as the main component, a silicone series polymer comprising polymethylsiloxane as the component, and a polyvinyl ether series polymer. In these elastomers, from the points of the purity, the thermoplastic property, the economy (cost), etc., it is preferred to use polyisobutyrene (preferably a mixture of that having a high molecular weight and that having a low molecular weight), an acrylic polymer (preferably having a number average molecular weight of 20,000 to 100,000 and a weight average molecular weight of 800,000 to 1,400,000), or a styrene/isoprene/styrene block copolymer (preferably having a weight average molecular weight of several hundred thousand), as the elastomer component.

The hygroscopic material which is contained in the pressure-sensitive adhesive layer together with the elastomer(s) is a material for preventing the occurrence of the cohesive failure of the pressure-sensitive adhesive layer by properly absorbing water such as moisture and sweat, etc., during attaching and leaving a part of the material containing water on the attached surface without leaving the elastomer(s) on the attached surface when detaching the preparation from the attached surface. For sufficiently obtaining the effect of the present invention, the hygroscopic material is contained in the pressure-sensitive adhesive layer in the range of from 5 to 50% by weight, and preferably from 20 to 40% by weight.

As such a hygroscopic material, not only a material which is dissolved by absorbing water but also a material which becomes a so-called jelly form by absorbing moisture or is called a water-absorbing polymer, can be used. For example, carboxymethyl cellulose sodium, carboxymethyl cellulose calcium, hydroxypropyl cellulose, guar gum, locust bean gum, xanthan gum, pectin, gelatin, sodium alginate, calcium alginate, carrageenan, collagen, and polyvinyl pyrrolidone can be used singly or as a mixture thereof. In these hydroscopic materials, from the points of a gel forming property and the hygroscopicity, carboxymethyl cellulose sodium, dextrin, pectin, and gelatin are preferably used.

In addition, the tape preparation of the present invention has a function of properly absorbing moisture during attaching by containing therein the foregoing hygroscopic material and in this case, it is preferred that the kind and amount of the hygroscopic material are selected such that the range of water absorption does not become more than 50%, with the lower limit being 3%, and preferably from 3 to 30% by weight of the weight of the pressure-sensitive adhesive layer before absorbing water. If the water absorption of the tape preparation is less than 3% such that the tape preparation scarcely absorbs water, at detaching the tape preparation from the skin surface, the possibility of peeling off and injuring the horny layer at the attached site is very high, whereby the desired effect of the present invention can not be obtained. Also, if the water absorption is over 50%, the possibility of causing a cohesive failure phenomenon wherein a large amount of the pressure-sensitive adhesive layer remains on the skin surface, at detaching the tape preparation from the skin surface is undesirably increased.

The water absorption (%) as used herein means a percentage obtained by dividing the difference of the weight of the drug-containing pressure-sensitive adhesive layer between after applying the tape preparation to the skin surface for 4 hours and before the application of the tape preparation, by the weight of the drug-containing pressure-sensitive adhesive layer before the application.

The drug-containing pressure-sensitive adhesive layer in the present invention is composed of at least the foregoing constituting materials but, if necessary, can properly contain a tackifier resin (for tackiness improvement), a polyvalent metal salt (for improvement of the cohesive force of the pressure-sensitive adhesive layer and the crosslinkage of the hygroscopic material), a percutaneous absorption accelerator (for improvement of the percutaneous absorption), various kinds of fillers (for shaping effect and weighting effect), etc.

In particular, in the optional compounding additives described above, as the percutaneous absorption accelerator for efficiently releasing the drug(s) from the drug-containing pressure-sensitive adhesive layer, for example, the following materials can be used.

(1) Straight chain, branched, or cyclic aliphatic hydrocarbons having from 5 to 30 carbon atoms which may be substituted with a halogen: The bromine- or chlorine-substituted aliphatic hydrocarbons are preferred, in the case of the straight chain aliphatic hydrocarbons, alkanes having from 5 to 30 carbon atoms, preferably from 6 to 24 carbon atoms, which may have one or two unsaturated bonds, are preferred, and in the case of the cyclic aliphatic hydrocarbons, monocyclic alkanes each having from 6 to 10 carbon atoms or bicyclic alkanes each having from 10 to 12 carbon atoms are preferred. The hydrocarbons may be substituted with at least one selected from the group consisting of a lower alkyl group (having 1 to 5 carbon atoms) and a lower alkenyl group (having 1 to 5 carbon atoms).

Specific examples thereof are n-pentane, n-hexane, n-heptane, n-octane, n-nonane, n-decane, n-undecane, n-dodecane, n-tetradecane, n-hexadecane, n-octadecane, 2-methylpentane, 2-methylhexane, 2,3-dimethylhexane, 2-methylnonane, 2,6-dimethyloctane, 2,2,4,4,6,8,8-heptamethylnonane, pristane, squalane, soft fluid paraffin, p-methane, limonene, the hydrogenated product of a limonene dimer, cyclohexane, 1,3-dimethylcyclohexane, cyclooctane, isobutylcyclohexane, cyclododecane, methyldecane, decalin, octyl bromide, decyl bromide, dodecyl bromide, hexadecyl bromide, dodecyl bromide, and dibromododecane.

(2) Alcohol esters of an aliphatic carboxylic acid having from 11 to 26 total carbon atoms: Esterified products of a fatty acid having from 10 to 20 carbon atoms, preferably from 12 to 18 saturated fatty acid and a monohydric alcohol having from 1 to 6 carbon atoms, such as methyl alcohol, ethyl alcohol, n-propyl alcohol, iso-propyl alcohol, n-butyl alcohol, iso-butyl alcohol, sec-butyl alcohol, t-butyl alcohol, n-amyl alcohol, iso-amyl alcohol, n-hexyl alcohol, etc., and specific examples of the alcohol esters are methyl laurate, ethyl laurate, hexyl laurate, isopropyl myristate, isopropyl palmitate, methyl stearate, and butyl stearate.

(3) Mono- or diethers having from 10 to 24 carbon atoms: Specific examples are alkyl monoethers such as dibutyl ether, dihexyl ether, dioctyl ether, didodecyl ether, methoxydodecane, ethoxydodecane, etc., alicyclic ethers such as 1,8-cineole, etc., and alkyl diethers such as ethylene glycol dibutyl ether, ethylene glycol dioctyl ether, etc.

(4) Ketones having from 11 to 15 carbon atoms: Specific examples are aliphatic ketones such as 2-undecanone, 3-undecanone, 4-undecanone, 5-undecanone, 6-undecanone, 3-dodecanone, 4-dodecanone, 5-dodecanone, 2-tridecanone, 3-tridecanone, 7-tridecanone, 8-pentadecanone, 3-hexadecanone, etc.

(5) Others: Specifically, there are azone, pyrrolidonecarboxylic acid lauryl ester, nicotinic acid lauryl ester, proline lauryl ester, etc.

The percutaneous absorption accelerators described above can be added singly or as a mixture thereof according to the purpose, and the addition amount thereof is preferably in the range of from about 0.5 to 20 parts by weight per 100 parts by weight of the sum total of the elastomer(s) and the hygroscopic material(s) mainly constituting the pressure-sensitive adhesive layer by considering the balance of the adhesive force and the cohesive force of the pressure-sensitive adhesive layer.

The present invention is now illustrated in greater detail by reference to the following examples which, however, are not to be construed as limiting the present invention in any way. Unless otherwise indicated, all parts are by weight.

EXAMPLES 1 to 12

As the fundamental formulation, 60 parts of each of the elastomers, 30 parts of each of the hygroscopic materials, and 10 parts of each of the percutaneous absorption drugs shown in Table 1 below were used.

First, the elastomer was kneaded by a kneader kept at 80° C. for 20 minutes and the hygroscopic material and the percutaneous absorption drug previously mixed was added to the kneaded elastomer and the resultant mixture was kneaded for 20 minutes at 80° C.

Thereafter, the mixture was cooled, placed between two polyester films each subjected to a silicone treatment, and press-molded (pressing condition: 80° C., 2 minutes, pressing pressure 100 kgf/cm$^2$).

Then, the polyester film at one side was peeled off, the remaining assembly was laminated onto a polyurethane film as a support, and the assembly was press-molded again (pressing condition: 80° C., one minute, pressing pressure 100 kgf/cm$^2$) to provide each percutaneous administration tape preparation of the present invention having a drug-containing pressure-sensitive adhesive layer having a thickness of 200 μm.

EXAMPLE 13

By following the same procedure as the case of Example 1 except that 50 part of the elastomer, 40 parts of the hygroscopic material, and 10 parts of the percutaneous absorption drug were used, a percutaneous administration tape preparation of the present invention was prepared.

EXAMPLE 14

By following the same procedure as the case of Example 1 except that 70 parts of the elastomer, 20 parts of the hygroscopic material, and 10 parts of the percutaneous absorption drug were used, a percutaneous administration tape preparation of the present invention was prepared.

COMPARATIVE EXAMPLES 1 to 3

By following the same procedure as Example 1 except that 90 parts of each of the elastomers and 10 parts of each of the percutaneous absorption drugs were used without using any hygroscopic material, each tape preparation was prepared.

COMPARATIVE EXAMPLES 4 and 5

By following the same procedure as Example 1 except that 87 parts of each of the elastomers, 3 parts of each of the hygroscopic materials, and 10 parts of each of the percutaneous absorption drugs were used, each tape preparation was prepared.

COMPARATIVE EXAMPLES 6 and 7

By following the same procedure as Example 1 except that 30 parts of each of the elastomers, 60 parts of each of the hygroscopic materials, and 10 parts of each of the percutaneous absorption drugs were used, each tape preparation were prepared.

The elastomers, the hygroscopic materials and the percutaneous absorption drugs used in the examples and comparative examples are shown in Table 1 below and when two kinds of the hygroscopic materials were used, each hygroscopic material was used in an equivalent amount.

TABLE 1

| Sample No. | Elastomer | Hygroscopic Material | Percutaneous Absorption Drug |
|---|---|---|---|
| Example 1 | Polyisobutylene[1] | Dextrin Pectin | Propranoiol hydrochloride |
| Example 2 | Acrylic Polymer[2] | CMC-Na[5] Gelatin | Propranolol hydrochloride |
| Example 3 | SIS[3] | CMC-Na[5] Dextrin | Propranolol hydrochloride |
| Example 4 | Polyisobutylene[1] | CMC-Na[5] | Indomethacin |
| Example 5 | Acrylic Polymer[2] | Gelatin | Indomethacin |
| Example 6 | SIS[3] | Dextrin Pectin | Indomethacin |
| Example 7 | Polyisobutylene[1] | Gelatin Pectin | Ketoprofen |
| Example 8 | Acrylic Polymer[2] | CMC-Na[5] Dextrin | Ketoprofen |
| Example 9 | SIS[3] | Dextrin Gelatin | Ketoprofen |
| Example 10 | Acrylic Polymer[4] | CMC-Na[5] Dextrin | Propranolol hydrochloride |
| Example 11 | Polyisobutylene[1] | Sumikagel[6] | Propranolol hydrochloride |
| Example 12 | Acrylic Polymer[2] | Sumikagel[6] | Indomethacin |
| Example 13 | Polyisobutylene[7] | Gelatin Pectin | Ketoprofen |
| Example 14 | Polyisobutylene[8] | Gelatin Pectin | Ketoprofen |
| Comparative Example 1 | Polyisobutylene[1] | — | Propranolol hydrochloride |
| Comparative Example 2 | Acrylic Polymer[2] | — | Indomethacin |
| Comparative Example 3 | SIS[3] | — | Ketoprofen |
| Comparative Example 4 | Acrylic polymer[2] | Gelatin | Propranolol hydrochloride |
| Comparative Example 5 | Poyisobutylene[1] | Pectin | Propranolol hydrochloride |
| Comparative Example 6 | Polyisobutylene[1] | Gelatin Pectin | Indomethacin |
| Comparative Example 7 | SIS[3] | CMC-Na[5] Dextrin | Indomethacin |

[1]High-molecular weight polyisobutylene(Vistanex LM80)/low-molecular weight polyisobutylene (Vistanex LMMH) = 1/3
[2]Octyl acrylate/acrylic acid = 95/5
[3]Styrene-isoprene-styrene copolymer/fluid paraffin/tackifier (Arkon P-100 produced by Arakawa Chemical Industry Ltd.) = 42/33/25
[4]octyl acrylate/vinylpyrrolidone = 75/25
[5]Carboxymethyl cellulose-sodium
[6]Water Absorbing Polymer, Sumikagel SP-520 (produced by Sumitomo Chemical Co., Ltd.)
[7]High-molecular weight polyisobutylene (Vistanex LM80)/low-molecular weight polyisobutylene (Vistanex LMMH) = 1/2

TABLE 1-continued

| Sample No. | Elastomer | Hygroscopic Material | Percutaneous Absorption Drug |
|---|---|---|---|

[8]High- molecular weight polyisobutylene (Vistanex LM80)/low-molecular weight polyisobutylene (Vistanex LMMH) = 1/5
All the ratios are by weight.

Each of the tape preparations prepared in the examples and the comparative examples described above, which had a 200 $\mu$m thick drug-containing pressure-sensitive adhesive layer, was cut into the size of 5 cm x 5 cm, applied to the skin surface of the man's brachium, and while observing the releasing state of the sample during attaching to evaluate each preparation in terms of skin adhesion, and after 4 hours since the application, the sample was released.

The state of the skin irritation was evaluated by visually observing the skin surface directly after applying each sample thereto, the state that the skin surface became red was evaluated to have a skin irritation, and the state showing no change before the application was evaluated to have no skin irritation.

Furthermore, from the difference between the weight of the drug-containing pressure-sensitive adhesive layer before the application to the skin surface described above and the weight thereof after the application, the absorbed amount of water by perspiration was obtained and the water absorption was calculated therefrom. Also, the skin surface from which the sample tape preparation had been released was wiped with cotton fabric having absorbed water to collected the residual components on the skin surface, and the components were confirmed.

The results obtained are shown in Table 2 below.

TABLE 2

| Sample No. | Skin Irritation | Residue | Skin Adhesion | Water Absorption (%) |
|---|---|---|---|---|
| Example 1 | none | observed[2] | good | 8.5 |
| Example 2 | none | observed[3,4] | good | 10.3 |
| Example 3 | none | observed[2,3] | good | 9.2 |
| Example 4 | none | observed[3] | good | 7.7 |
| Example 5 | none | observed[4] | good | 9.6 |
| Example 6 | none | observed[2] | good | 7.5 |
| Example 7 | none | observed[4] | good | 8.7 |
| Example 8 | none | observed[2,3] | good | 9.1 |
| Example 9 | none | observed[2,4] | good | 8.4 |
| Example 10 | none | observed[2,3] | good | 10.0 |
| Example 11 | none[1] | — | good | 10.5 |
| Example 12 | none[1] | — | good | 10.8 |
| Example 13 | none[1] | observed[4] | good | 7.5 |
| Example 14 | none[1] | observed[4] | good | 8.3 |
| Comparative Example 1 | observed | none | partially peeled | 0.4 |
| Comparative Example 2 | observed | none | partially peeled | 0.2 |
| Comparative Example 3 | observed | none | partially peeled | 0.2 |
| Comparative Example 4 | observed | none | partially peeled | 0.2 |
| Comparative Example 5 | observed | none | partially peeled | 0.2 |
| Comparative Example 6 | none | observed[4] | peeled[5] | — |
| Comparative Example 7 | none | observed[2,3] | peeled[5] | — |

[1]The cohesive failure of the pressure-sensitive adhesive layer was observed.
[2]The reaction (blue green color to dark blue green color) originated in dextran was shown by an anthrone reaction.

TABLE 2-continued

| Sample No. | Skin Irritation | Residue | Skin Adhesion | Water Absorption (%) |
|---|---|---|---|---|

[3])The reaction (brown cotton-form precipitations) originated in CMC was shown by a ferric chloride reagent.
[4])The reaction (the liquid became turbid) originated in gelatin was shown by a tannic acid reagent.
[5])The pressure-sensitive adhesive layer remained on the skin surface by the cohesive failure thereof.

Since the percutaneous administration tape preparation of the present invention is formed by a specific amount of the elastomer and the hygroscopic material and contains percutaneous absorption drug uniformly dispersed in the pressure-sensitive adhesive layer thereof, the hygroscopic material is partially remains on the skin surface at detaching the tape preparation by properly absorbing sweet, etc., during attaching onto the skin surface to reduce the skin irritation.

Accordingly, since the tape preparation of this invention keeps an excellent skin adhesion at attaching to the skin surface and shows a low skin irritation without giving injury the horny layer at detaching it from the skin surface, the tape preparation of the present invention is very practically useful.

While the invention has been described in detail with reference to specific embodiments, it will be apparent to one skilled in the art that various changes and modifications can be made to the invention without departing from its spirit and scope.

What is claimed is:

1. A percutaneous administration tape preparation composed of a sheet-form support, a drug-containing pressure-sensitive adhesive layer, and a separator, wherein the drug-containing pressure-sensitive adhesive layer comprises a uniform dispersed state containing from 50 to 95% by weight one or more kinds of elastomers, from 5 to 50% by weight a hygroscopic material, and a percutaneous absorption drug so that a part of the hygroscopic material contained therein remains on the applied surface at detaching the tape preparation from the applied surface, and wherein said hygroscopic material absorbs from 3 to 30 wt. % water based on a water-free weight of said pressure-sensitive adhesive layer.

2. A percutaneous administration tape preparation of claim 1, wherein the elastomer is selected from polyisobutylene, an acrylic polymer, and a styrene/isoprene/styrene block copolymer.

3. A percutaneous administration tape preparation of claim 1, wherein the hygroscopic material is at least one selected from carboxymethyl cellulose sodium, dextrin, pectin, and gelatin.

* * * * *